(12) United States Patent
Arita et al.

(10) Patent No.: US 6,313,343 B1
(45) Date of Patent: Nov. 6, 2001

(54) PROCESS FOR THE PREPARATION OF ALPHA-OXOALDEHYDES

(75) Inventors: Yoshitaka Arita, Nishinomiya; Akihiko Ohta, Suita; Noboru Saito, Takatsuki; Kimio Ariyoshi, Suita, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/462,527

(22) PCT Filed: May 19, 1999

(86) PCT No.: PCT/JP99/02633

§ 371 Date: Jan. 7, 2000

§ 102(e) Date: Jan. 7, 2000

(87) PCT Pub. No.: WO99/59948

PCT Pub. Date: Nov. 25, 1999

(30) Foreign Application Priority Data

May 20, 1998 (JP) .................................................. 10-138869

(51) Int. Cl.⁷ .................................................. C07C 69/66
(52) U.S. Cl. .......................... 560/177; 568/449; 568/471; 568/472; 568/473
(58) Field of Search ............................ 560/177; 568/449, 568/471, 472, 473

(56) References Cited

U.S. PATENT DOCUMENTS 5,750,768   5/1998   Arita et al. ........................... 560/177

FOREIGN PATENT DOCUMENTS

| 85100530 | 3/1986 | (CN) . |
|---|---|---|
| 52-17408 | 2/1977 | (JP) . |
| 58-38227 | 3/1983 | (JP) . |
| 58-59933 | 4/1983 | (JP) . |
| 58-124730 | 7/1983 | (JP) . |
| 60-199846 | 10/1985 | (JP) . |
| 61-54011 | 11/1986 | (JP) . |
| 3-41046 | 2/1991 | (JP) . |
| 3-232835 | 10/1991 | (JP) . |
| 8-32648 | 3/1996 | (JP) . |
| 09-118650 | 5/1997 | (JP) . |
| 09-268156 | 10/1997 | (JP) . |

OTHER PUBLICATIONS

"Oxidative dehydrogenation of glycol to glyoxal on a P–modified electrolytic silver catalyst", J. Deng, et al. Catalysis Letters 36 (1996), pp. 207–214.

*Primary Examiner*—Sreeni Padmanabhan
(74) *Attorney, Agent, or Firm*—David G. Conlin; John B. Alexander; Edwards & Angell, LLP

(57) ABSTRACT

Alkylene glycol is oxidized in a vapor phase in the presence of alcohol (a), oxygen, and a catalyst (a) (primary reaction). α-oxoaldehyde, and alcohol (b) or olefin, are oxidized in a vapor phase in the presence of oxygen and a catalyst (b) (secondary reaction). A molar ratio of the alkylene glycol to the alcohol (a) is preferably in a range of 1/100 to 5/1. It is preferable that one same compound is used as the alcohol (a) and the alcohol (b). In the case where the primary and secondary reactions are successively executed, a reaction device in which a primary reactor and a secondary reactor are connected in a two-stage connection type is preferably used. This ensures that a method is provided that is capable of producing α-oxoaldehyde at a higher yield than conventionally, and further, that is capable of stably obtaining an α-oxoaldehyde solution or gas with a higher concentration than conventionally.

10 Claims, 1 Drawing Sheet

US 6,313,343 B1

PROCESS FOR THE PREPARATION OF ALPHA-OXOALDEHYDES

This is the U.S. National Stage Application of PCT/JP99/02633 filed May 19, 1999.

TECHNICAL FIELD

The present invention relates to a method of production of α-oxoaldehyde by vapor phase reaction, and a method of production of α-oxocarboxylate by vapor phase reaction.

Glyoxal and pyruvic aldehyde (methyl glyoxal) as typical α-oxoaldehyde are chemical compounds very useful in industrial fields, used as various products such as a fiber processing agent, a paper processing agent, a soil hardening agent, or as intermediate materials for various products. Further, glyoxylate as typical α-oxocarboxylate is an industrially useful chemical compound: for example, sodium polyacetal carboxylate, which is obtained from polymer of glyoxylate, is used as a builder for detergents and the like. Further, glyoxylic acid obtained by hydrolysis of glyoxylate is a very useful compound especially for intermediate materials of various products such as medical products, cosmetics, perfumes, and agricultural chemicals.

BACKGROUND ART

Conventionally, a method of production of α-oxoaldehyde by oxidative dehydrogenation of alkylene glycol in the presence of a silver catalyst has been known. For example, the following methods are known: a method of obtaining glyoxal at a yield in the 60% order by oxidative dehydrogenation of ethylene glycol, which is the simplest alkylene glycol, with use of metallic silver (silver crystal) as a catalyst, whose particle diameter is in a range of 0.1 mm to 2.5 mm (the Japanese Examined Patent Publication 54011/1986 (Tokukosho 61-54011, Date of Publication: Nov. 20, 1986); and, a method of obtaining glyoxal at a yield of, for example, 82% by oxidative dehydrogenation of ethylene glycol with use, as a catalyst, of metallic silver modified with a phosphorus-containing compound (the Japanese Publication for Laid-Open Patent Application No. 38227/1983 [Tokukaisho 58-38227, Date of Publication: Mar. 5, 1983], the Japanese Publication for Laid-Open Patent Application No. 59933/1983 [Tokukaisho 58-59933, Date of Publication: Apr. 9, 1983], the Chinese Patent No. 85100530 [Date of Publication: Apr. 1, 1985], Catalysis letters, 36(1996) 207–214 [received Jul. 10, 1995, Accepted Oct. 11, 1995]). Also known are: a method of obtaining glyoxal at a yield of 84% by oxidative dehydrogenation of ethylene glycol to which a vaporized phosphorus-containing compound has been added, with use of a granulated metallic silver as a catalyst (the Japanese Publication for Laid-Open Patent Application No.232835/1991 [Tokukaihei 3-232835, Date of Publication: Oct. 16, 1991]); and, a method of obtaining glyoxal at a yield in the 70% order by oxidative dehydrogenation of ethylene glycol with use of, as a catalyst, metallic silver carried by a carrier such as silicon carbide or silicon nitride (The Japanese Examined Patent Publication No.32648/1996 [Tokukohei 8-32648, Date of Publication: Mar. 29, 1996]). In these methods, since glyoxal highly tends to be polymerized, a lot of water (1–3.5 times of ethylene glycol in molarity) is supplied (together with other materials) to a reaction system, so that glyoxal produced is taken out in, for example, a 40-percent-by-weight (wt %) aqueous solution state, as a manufactured product.

The foregoing methods, however, cannot be regarded as methods capable of producing glyoxal at a sufficiently high yield and at a high concentration.

On the other hand, the inventors of the present invention, etc., have proposed, as a method of producing α-oxocarboxylate from α-oxoaldehyde, a method wherein α-oxoaldehyde and alcohol as materials are oxidative-esterified with use of oxygen and a catalyst (the Japanese Publication for Laid-Open Patent Application No.118650/1997 [Tokukaihei 9-118650, Date of Publication: May 6, 1997]). By the foregoing method, by, for example, heating 40 wt % aqueous solution of glyoxal as the simplest α-oxoaldehyde available in the market, glyoxal in a gaseous state is obtained as a material. To supply vaporized glyoxal to a reaction system, however, sometimes involves difficulties from the viewpoint of industrial application, since the polymerizability of glyoxal is very high. Besides, it follows that glyoxylate as α-oxocarboxylate is obtained in the presence of water in the reaction system, and hence, glyoxylate is sometimes hydrolyzed thereby, possibly along with other factors, causing the yield to decrease.

In other words, the foregoing conventional methods have a drawback of being incapable of producing α-oxoaldehyde at a high yield. Further, the same have a drawback of being incapable of stably obtaining a high-concentration α-oxoaldehyde solution or gas. Moreover, because of these drawbacks involved in the foregoing methods, there further arises a problem that it is impossible to produce α-oxocarboxylate at a high yield.

The present invention has been made in light of the foregoing conventional problems, and an object of the present invention is to provide a method wherein α-oxoaldehyde, at a higher concentration than conventionally, in a solution state or in a gaseous state, can be stably produced at a higher yield than conventionally. Another object of the present invention is to provide a method wherein α-oxocarboxylate is produced at a higher yield than conventionally.

DISCLOSURE OF THE INVENTION

The inventors eagerly studied a method of production of α-oxoaldehyde and a method of production of α-oxocarboxylate, in order to achieve the above object. As a result, it was found that α-oxoaldehyde could be produced at a higher yield than conventionally by vapor phase oxidation of alkylene glycol in the presence of alcohol (a), oxygen, and a catalyst, and besides, α-oxoaldehyde solution or gas could be stably obtained at a higher concentration than conventionally. Further, it was also found that α-oxocarboxylate could be produced at a higher yield than conventionally by vapor phase oxidation of the α-oxoaldehyde obtained by the foregoing method and, for example, alcohol (b) in the presence of oxygen and a catalyst. The present invention was completed based on these findings.

More specifically, to achieve the aforementioned object of the present invention, a method of production of α-oxoaldehyde in accordance with the present invention is characterized in that alkylene glycol is oxidized in a vapor phase in the presence of alcohol (a), oxygen, and catalyst. Further, the method of production of α-oxoaldehyde in accordance with the present invention is characterized in that a molar ratio of alkylene glycol to alcohol (a) is in a range of 1/100 to 5/1.

To achieve the aforementioned object of the present invention, a method of production of α-oxocarboxylate in accordance with the present invention is characterized by including the steps of oxidizing alkylene glycol in a vapor phase in the presence of alcohol (a), oxygen, and a catalyst so as to obtain α-oxoaldehyde, and thereafter oxidizing the α-oxoaldehyde, and alcohol (b) or olefin, in a vapor phase in the presence of oxygen and a catalyst. Further, the method of production of α-oxocarboxylate in accordance with the present invention is characterized in that one and same compound is used as the alcohol (a) and the alcohol (b). Moreover, the method of production of α-oxocarboxylate in accordance with the present invention is characterized in that the alcohol (a) contains unreacted alcohol (b) that is contained in reactant gas resultant from vapor phase oxidation of α-oxoaldehyde and alcohol (b).

For a fuller understanding of the nature and advantages of the invention, reference should be made to the ensuing detailed description taken in conjunction with the accompanying drawings.

BEST MODE FOR CARRYING OUT THE INVENTION

Figure 1:
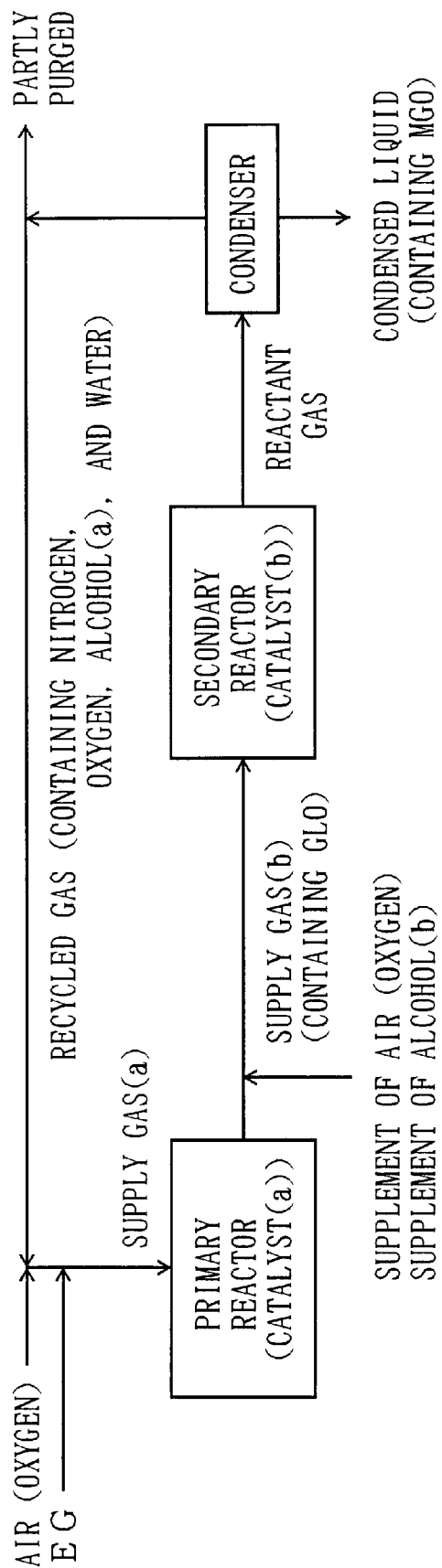
FIG. 1 is a block diagram schematically illustrating a device for and a process of reaction in Example 19.

A method of production of α-oxoaldehyde in accordance with the present invention is a method of vapor phase oxidation of alkylene glycol in the presence of alcohol (a), oxygen (molecular state), and a catalyst. A method of production of α-oxocarboxylate in accordance with the present invention is a method of vapor phase oxidation, i.e., oxidative esterification, of α-oxoaldehyde obtained by the foregoing method, and alcohol (b) or olefin, in the presence of oxygen (molecular state) and a catalyst. Incidentally, in the following descriptions, for conveniences' sake, the reaction wherein α-oxoaldehyde is obtained by vapor phase oxidation of alkylene glycol is referred to as primary reaction, while the reaction wherein α-oxocarboxylate is obtained by oxidative esterification of α-oxoaldehyde is referred to as secondary reaction. Further, the catalyst used in the vapor phase oxidation of alkylene glycol is referred to as catalyst (a), while the catalyst used in the oxidative esterification of α-oxoaldehyde is referred to as catalyst (b).

The foregoing alkylene glycol used as material is not specifically limited, but a compound which vaporizes at a normal pressure (atmospheric pressure) is preferable, and 1,2-diol expressed by the formula (1) below is more preferable:

(1)

where R is a hydrogen atom or an organic residue. Concrete examples of the 1,2-diol include: ethylene glycol in which a substituent represented by R is a hydrogen atom; 1,2-diol in which a substituent represented by R is a saturated aliphatic hydrocarbon group with 1 to 4 carbon atoms, such as propylene glycol, 1,2-butanediol, 1,2-pentanediol, 1,2-hexanediol, 3-methyl-1,2-butanediol, 3-methyl-1,2-pentandiol, or 4-methyl-1,2-pentandiol; 1,2-diol in which a substituent represented by R is an unsaturated aliphatic hydrocarbon group with 2 to 3 carbon atoms, such as 1,2-dihydroxy-3-butene, 1,2-dihydroxy-3-pentene, or 1,2-dihydroxy-4-pentene; and, 1,2-diol in which a substituent represented by R is an aromatic hydrocarbon group, such as 1-phenyl-1,2-dihydroxyethane. The 1,2-diol, however, is not particularly limited. Among the foregoing 1,2-diols, ethylene glycol and propylene glycol are particularly preferable. In other words, 1,2-diol with 2 to 3 carbon atoms are particularly preferable as alkylene glycol.

Concrete examples of alcohol (a) subjected to the primary reaction, that is, alcohol (a) supplied (together with other materials) to a reaction system, include: aliphatic alcohol having 1~18 carbon atoms that is industrially available with ease, such as methanol, ethanol, 1-propanol, 2-propanol, 1-butanol, 2-butanol, iso-butanol, tert-butanol, hexanol, cyclohexanol, octanol, 2-ethylhexanol, lauryl alcohol, and stearyl alcohol. The alcohol (a), however, is not particularly limited. One of these may be used, or alternatively, not less than two selected therefrom may be used in combination. Among the above-listed examples, aliphatic alcohol having 1 to 4 carbon atoms, such as methanol, ethanol, 1-propanol, 2-propanol, 1-butanol, 2-butanol, iso-butanol, or tert-butanol is preferable, and a methanol is more preferable.

A ratio of alcohol (a) to alkylene glycol, i.e., a molar ratio of alcohol (a) to alkylene glycol, may be set in accordance with combination of the two, reaction conditions, etc., and is not particularly limited. It is, however, preferably in a range of 1/100 to 5/1, or more preferably in a range of 1/50 to 5/1, or further, particularly preferably in a range of 1/25 to 3/1. By setting the molar ratio of the two in the foregoing range, α-oxoaldehyde can be produced at a higher yield. Further, by setting a ratio of alcohol (a) to alkylene glycol lower but in the foregoing range, an α-oxoaldehyde solution or gas with a higher concentration than conventionally can be stably obtained.

Though the catalyst (a) used in the primary reaction is not particularly limited, examples of the catalyst (a) include metallic catalysts such as metallic silver, and various oxide catalysts such as CuO—ZnO/α-Al$_2$O$_3$, and Ag$_2$O—SiO$_2$—ZnO. More concretely, metallic silver (electrolytic silver), and metallic silver (electrolytic silver) modified with a phosphorus-containing component such as phosphoric acid are preferable. As a form of the catalyst (a), various types including a granulated type and a reticulate type are applicable, but it is not particularly limited. A diameter thereof in the case where the catalyst (a) is in a granulated form is, though not particularly limited, preferably in a range of 8 to 60 mesh. Incidentally, the method of preparation of the catalyst (a) is not particularly limited, but use of metallic silver available from the market, which has a predetermined uniform particle diameter, is easy and convenient in the case where a granulated metallic silver is to be used as the catalyst (a).

The primary reaction is a reaction through which gaseous α-oxoaldehyde is obtained from alkylene glycol, which can be executed in accordance with any one of various known methods of production of α-oxoaldehyde. A reactor (device) used in the primary reaction may be anything as long as it is capable of vapor phase oxidation, and it is not particularly limited though a fixed-bed flow-through-type vapor phase reactor, for example, is preferable. In the case where the fixed-bed flow-through-type vapor phase reactor is used as the reactor while granulated metallic silver is used as the catalyst (a), it is preferable that the catalyst (a) is placed (accumulated) in the fixed-bed flow-through-type vapor phase reactor so that the particle diameter becomes greater from the gas inlet side to the gas outlet side in the reactor. More specifically, for example, the catalyst (a) placed in the gas inlet side in the reactor preferably has a diameter in a range of 16 to 60 mesh, or more preferably in a range of 20 to 30 mesh. On the other hand, the catalyst (a) placed in the gas outlet side in the reactor preferably has a diameter in a range of 8 to 30 mesh, or more preferably, in a range of 10 to 20 mesh. By thus placing (accumulating) the catalyst (a) in a fixed-bed flow-through-type vapor phase reactor, the yield of α-oxoaldehyde can be further improved.

With regard to oxygen subjected to the primary reaction, apart from oxygen gas, air, or a mixed gas resultant from diluting oxygen gas or air with use of an inactive gas such as nitrogen gas or helium gas may be applicable. From industrial viewpoint, air or a mixed gas of air and an inactive gas is preferably used as a source of oxygen since it is inexpensive.

A composition of the gas subjected to the primary reaction, that is, a gas containing alkylene glycol and alcohol (a) (hereinafter referred to as a supply gas (a)) is not particularly limited, but proportions of alkylene glycol, oxygen (oxygen gas), and alcohol (a) in the supply gas (a) are preferably, in this order, 1 percent by volume (vol %) to 10 vol %, 1 vol % to 10 vol %, and 0.01 vol % to 30 vol %, respectively (the inactive gas accounts for the rest, and the total is 100 vol %), or more preferably, 3 vol % to 8 vol %, 3 vol % to 8 vol %, and 0.01 vol % to 20 vol %, respectively (the same as the above applies). In the case where the composition of the supply gas (a) is out of the above-described range, α-oxoaldehyde might not be produced at a yield higher than conventionally. For example, in the case where the proportion of alkylene glycol is too high, a side reaction such as combustion tends to occur, thereby possibly making it impossible to control the primary reaction.

Further, the supply gas (a) may, as required, contain water (steam). A proportion of water in the case where the supply gas (a) contains water is preferably not more than 30 vol %, or more preferably not more than 10 vol %. Incidentally, the method of preparation of the supply gas (a) is not particularly limited.

To further improve the yield of α-oxoaldehyde, a phosphorus-containing compound may be present in the reaction system, or in other words, a vaporized phosphorus-containing compound may be added to the supply gas (a) as required. Examples of the phosphorus-containing compound include organic phosphorus-containing compounds such as triethyl phosphite, and diethyl phosphate, but anything may be used as the foregoing compound, provided that it is vaporized under the reaction conditions of the primary reaction. An amount of the phosphorus-containing compound added is not particularly limited, but a ratio of the phosphorus to alkylene glycol is preferably not more than 1 percent by weight (wt %), or more preferably not less than 40 ppm and not more than 100 ppm. Incidentally, in the case where metallic silver modified with use of a phosphorus-containing compound is used as the catalyst (a), addition of the foregoing phosphorus-containing compound in the reaction system is unnecessary.

The reaction conditions of the primary reaction is not particularly limited, as long as the same may be set depending on a composition of the supply gas (a), a type of the catalyst (a), a structure of the reactor, etc., so that the primary reaction can be controlled. The reaction temperature, however, is preferably set in a range of 400° C. to 700° C., or more preferably in a range of 500° C. to 650° C. Further, a space velocity (SV) is preferably in a range of 5,000 hr$^{-1}$ to 800,000 hr$^{-1}$, or more preferably in a range of 10,000 hr$^{-1}$ to 200,000 hr$^{-1}$. In the case where the space velocity is lower than 5,000 hr$^{-1}$, a side reaction like combustion may easily occur. In the case where the space velocity is higher than 800,000 hr$^{-1}$, a degree of conversion of alkylene glycol may possibly decrease.

For example, in the case where metallic silver as the catalyst (a) is placed in the fixed-bed flow-through-type vapor phase reactor and the primary reaction under the foregoing reaction conditions with use of the supply gas (a) containing ethylene glycol as alkylene glycol, prepared so as to have a composition ratio in the foregoing range, is caused to take place, glyoxal as α-oxoaldehyde is obtained at an yield of about 80% to 95%, with a degree of conversion of ethylene glycol of about 99% to 100%. Incidentally, the space velocity is an equivalent in the normal temperature and pressure state (N.T.P.) of a value obtained by dividing an amount (L/hr) of the supply gas (a) supplied per one hour with an amount (L) of the catalyst (a) used in the primary reaction.

As a result of the above-described reaction, a reactant gas containing gaseous α-oxoaldehyde is obtained. A proportion of α-oxoaldehyde in the reactant gas may be set, represented as a concentration of α-oxoaldehyde in a solution obtained by condensing the reactant gas, in a range of 45 wt % to 80 wt %, or further, 50 wt % to 70 wt %, by appropriately setting the reaction conditions of the primary reaction. In other words, α-oxoaldehyde can be produced at a higher yield than conventionally, and an α-oxoaldehyde solution or gas at a higher concentration than conventionally can be obtained stably. Further, since higher-concentration α-oxoaldehyde solution than conventionally can be easily obtained, costs for transport and storage can be reduced. A method for collection and isolation of α-oxoaldehyde are not particularly limited, and various known methods are applicable. Not α-oxoaldehyde isolated from the reactant gas, but the reactant gas containing α-oxoaldehyde can be used as it is, in the secondary reaction.

In the case where 1,2-diol expressed by the aforementioned formula (1) is used as alkylene glycol, α-oxoaldehyde expressed by a formula (2) below is obtained:

(2)

where R represents a hydrogen atom or an organic residue. Though α-oxoaldehyde is not particularly limited, concrete examples of α-oxoaldehyde include: glyoxal in that a substituent represented by R is a hydrogen atom; α-oxoaldehyde in that a substituent represented by R is a saturated aliphatic hydrocarbon group with 1 to 4 carbon atoms, such as pyruvic aldehyde, 2-oxobutanal, 2-oxopentanal, 2-oxohexanal, 3-methyl-2-oxobutanal, 3-methyl-2-oxopentanal, or 4-methyl-2-oxopentanal; α-oxoaldehyde in that a substituent represented by R is an unsaturated aliphatic hydrocarbon group of 2 to 3 carbon atoms, such as 2-oxo-3-butenal, 2-oxo-4-pentenal, or 2-oxo-3-pentenal; α-oxoaldehyde in that a substituent represented by R is an aromatic hydrocarbon group, such as 2-phenyl-2-oxoethanal. According to the method of the present invention, glyoxal is obtained from ethylene glycol, while pyruvic aldehyde (methyl glyoxal) is obtained from propylene glycol.

Incidentally, the reactant gas containing α-oxoaldehyde contains formaldehyde, carbon monoxide, carbon dioxide, water, etc. as by-products that are produced by side reaction like combustion. Though a part of alcohol (a) added is lost by side reaction such as combustion, about 90 wt % of the same is recovered, while about 10 wt % is converted to formaldehyde.

The detailed reason why the presence of alcohol (a) stabilizes α-oxoaldehyde in the primary reaction, that is, enables production of α-oxoaldehyde at a higher yield than in the conventional cases is unknown, but it is presumed that it is because α-oxoaldehyde, along with alcohol (a), forms hemiacetal.

Concrete examples of the aforementioned alcohol (b) subjected to the secondary reaction include alcohols applicable as the foregoing alcohol (a), and aromatic alcohols such as phenol and benzyl alcohol, though the alcohol (b) is not particularly limited. One of these may be used, or alternatively, not less than two selected therefrom may be used in combination. Among the above-listed examples, aliphatic alcohol having 1 to 4 carbon atoms, such as methanol, ethanol, 1-propanol, 2-propanol, 1-butanol, 2-butanol, iso-butanol, or tert-butanol is preferable, and methanol is more preferable.

Then, to enable the foregoing alcohol (a) to be applied as the alcohol (b), it is most preferable that one and same chemical compound is used as the alcohols (a) and (b). In other words, alcohol to be used as the alcohol (b) in the secondary reaction is preferably used as the alcohol (a) in the primary reaction. In this case, alcohol (a) need not be removed from α-oxoaldehyde prior to the secondary reaction. Furthermore, alcohol that is contained in a reactant gas resultant from the secondary reaction, remaining therein uncollected upon collection (separation) of α-oxocarboxylate and other produced matters from the reactant gas, can be applied, as it is, as alcohol (a) for the primary reaction. This makes the production of α-oxocarboxylate further easier.

Concrete examples of the aforementioned olefin subjected to the secondary reaction include those having 2 to 4 carbon atoms, such as ethylene, propylene, 1-butene, 2-butene, and isobutene, though olefin is not particularly limited. One of these olefins may be used, or alternatively, not less than two selected therefrom may be used in combination as required.

A ratio of alcohol (b) or olefin (hereinafter simply referred to as alcohol (b)) to α-oxoaldehyde, that is, a molar ratio of alcohol (b) to α-oxoaldehyde, may be preferably equivalent (1/1) in stoichiometry, but it may be set depending on combination of the two, reaction conditions, etc., and is not particularly limited.

Examples of the catalyst (b) used in the secondary reaction include metallic catalysts such as metallic silver, and other various catalysts based on oxides. Among these examples, a catalyst containing a phosphorus-containing inorganic oxide is preferable. The phosphorus-containing inorganic oxide is not particularly limited, as various chemical compounds are applicable as the same, but metallic phosphate and phosphorus-containing heteropolyacid are preferable. Note that a mixture of metallic phosphate and phosphorus-containing heteropolyacid can be used as catalyst (b).

The kinds of metal of metallic phosphate are not limited as long as phosphate can be produced. Examples of such metal include: alkali metal, alkaline earth metal, B, Al, Ti, V, Cr, Mn, Fe, Co, Ni, Zn, Zr, Mo, Pd, Ag, Cd, Sn, Pb, etc. One kind of metal selected therefrom may be contained in metallic phosphate, or alternatively, not less than two selected therefrom may be contained in metallic phosphate. In other words, metallic phosphate may contain not less than two kinds of metal. Further, not less than two kinds of metallic phosphate may be used in combination. In other words, examples of metallic phosphate as catalyst (b) include: metallic phosphate containing one type of metal; metallic phosphate containing not less than two types of metal; and a mixture of not less than two kinds of such metallic phosphate. Further, it is possible to place different kinds of metallic phosphate as catalyst (b), respectively on the gas inlet side and the gas outlet side in the reactor used in the secondary reaction.

A molar ratio of the metal to phosphorus in metallic phosphate does not necessarily agree with stoichiometric mixture ratio of orthophosphate, but is preferably approximate to the stoichiometric mixture ratio, and more specifically, preferably in a range of 1/0.5 to 1/2.

A method of preparation of metallic phosphate is not particularly limited, and examples of the same include various known methods such as: a coprecipitation method wherein metallic phosphate is coprecipitated in an aqueous solution obtained by mixing and dissolving a metallic salt and a phosphorus source; and a kneading method wherein a metallic salt and a phosphorus source are mixed and formed in a slurry form, and thereafter, kneaded so that metallic phosphate is obtained. Alternatively, as the foregoing metallic phosphate, a reagent available from the market can be used. Examples of the metallic salt include nitrate, carbonate, oxalate, hydroxide, and chloride, though the metallic salt is not particularly limited. Any one selected therefrom may be used, or alternatively, not less than two selected therefrom may be used in combination. Examples of the phosphorus source include phosphate such as orthophosphate, ammonium phosphate, diammonium hydrogenphosphate, or ammonium dihydrogenphosphate, though the phosphorus source is not particularly limited. Any one phosphorus source selected therefrom may be used, or alternatively, not less than two selected therefrom may be used in combination. A combination of the metallic salt and the phosphorus source is not particularly limited, and various combinations thereof are applicable.

Though depending on a kind and composition of metallic phosphate, the metallic phosphate is preferably dried in air at a temperature in a range of 100° C. to 120° C., calcined in air at a temperature in a range of 300° C. to 1000° C., or more preferably in a range of 400° C. to 800° C., and further, preferably subjected to a pre-processing operation such as molding or granulating to make the particle diameter uniform, according to necessity. Incidentally, metallic phosphate can be used as catalyst (b) without pre-processing.

Furthermore, the metallic phosphate in combination with an inorganic oxide, in a state of a mixture of the same, is preferably used as the catalyst (b). Examples of inorganic oxide include silica, titania, zirconia, niobium oxide, and diatomaceous earth, but the inorganic oxide is not particularly limited. For the titania, both anatase type and rutile type may be used. Any one inorganic oxide selected therefrom may be used, or alternatively, not less than two selected therefrom may be used in combination. An amount of inorganic oxide to be mixed in the metallic phosphate varies depending on the kind and composition of metallic phosphate, and the kind of the inorganic oxide. However, a proportion of the inorganic oxide in the total amount of metallic phosphate and the inorganic oxide is preferably in a range of 1 wt % to 90 wt %, more preferably, 10 wt % to 60 wt %. Note that metallic phosphate as it is can be used as catalyst (b), without being mixed with an inorganic oxide as described above.

The phosphorus-containing heteropolyacid is not particularly limited. However, Keggin type heteropolyacid expressed by the following formula is preferable because of its excellent function as a catalyst:

$$H_aPM_{12}O_{40} \cdot nH_2O$$

wherein M is a metal element of at least one selected from the group consisting of tungsten, molybdenum and vanadium, a is a numerical value determined by M, and n is 0 or a positive integer.

Further, the Keggin-type heteropolyacid in that a part or all of H is substituted with metal such as alkali metal, alkaline earth metal, and transition metal, that is, heteropolyacid salt expressed by the following formula, can be used:

$$H_{(a-b)}M'_bPM_{12}O_{40} \cdot nH_2O$$

wherein M is a metal element of at least one selected from the group consisting of tungsten, molybdenum and vanadium, M' is a metal element such as an alkali metal, alkaline earth metal, transition metal, etc., a is a numerical value determined by M, b is a numerical value selected at random from the range of $0<b\leq a$, and n is 0 or a positive integer. A method of preparation of Keggin type heteropolyacid or heteropolyacid salt, that is, a method of preparation of the foregoing phosphorus-containing heteropolyacid, is not particularly limited, and any one of various known methods is applicable.

Though depending on a type and composition of the phosphorus-containing heteropolyacid, the phosphorus-containing heteropolyacid is preferably dried in air and thereafter calcined in air prior to the secondary reaction at higher temperature than the reaction temperature of the secondary reaction. Note that, however, the phosphorus-containing heteropolyacid may be used as catalyst (b) without applying thereto the foregoing treatment.

Further, it is preferable to use as catalyst (b) the phosphorus-containing heteropolyacid in a state of being carried on a carrier. Concrete examples of such a carrier include silica, titania, zirconia, niobium oxide, and diatomaceous earth, but anything is applicable as the carrier, provided that it does not have adverse effects on the secondary reaction and is stable against phosphorus-containing heteropolyacid. For the titania, both the anatase type and the rutile type are applicable. Any one carrier may be used alone, or alternatively, not less than two carriers may be used in combination. The method of making the carrier carry phosphorus-containing heteropolyacid is not particularly limited, and a so-called kneading method, or the impregnating supporting method may be adopted. Note that phosphorus-containing heteropolyacid can be adopted alone so as to be used as catalyst (b), without being carried on a carrier.

The secondary reaction is a reaction through which gaseous α-oxocarboxylate is obtained from α-oxoaldehyde, which can be executed in accordance with any one of various known reactions of oxidation and oxidative esterification. A reactor (device) used in the secondary reaction is not particularly limited as long as it is capable of oxidative esterification, though a fixed-bed flow-through-type vapor phase reactor, for example, is preferable.

With regard to oxygen used in the secondary reaction, apart from oxygen gas, air, or a mixed gas obtained by diluting oxygen gas or air with use of an inactive gas such as nitrogen gas or helium gas, may be applicable. From industrial viewpoint, air or a mixed gas of air and an inactive gas is preferably used as a source of oxygen since it is inexpensive.

A composition of the gas subjected to the secondary reaction, that is, a gas containing α-oxoaldehyde and alcohol (b) (hereinafter referred to as a supply gas (b)) is not particularly limited, but proportions of α-oxoaldehyde, oxygen (oxygen gas), and alcohol (b) in the supply gas (b) are preferably, in this order, 1 to 10 vol %, 1 to 10 vol %, and 5 to 50 vol % (the inactive gas accounts for the rest, and the total is 100 vol %). In the case where the composition of the supply gas (b) is out of the above-described range, α-oxocarboxylate might not be produced at a yield higher than conventionally, and an amount of recovered alcohol (b) might increase. Further, the supply gas (b) may, as required, contain water (steam) produced (as by-product) in the primary reaction. Incidentally, a method of preparation of the supply gas (b) is not particularly limited.

The reaction conditions of the secondary reaction are not particularly limited as long as the same may be set depending on the composition of the supply gas (b), the type of the catalyst (b), the structure of the reactor, etc., so that the secondary reaction can be controlled. The reaction temperature, however, is preferably set in a range of 150° C. to 500° C., or more preferably in a range of 180° C. to 400° C. Further, a space velocity (SV) is preferably in a range of 100 hr$^{-1}$ to 10,000 hr$^{-1}$, or more preferably in a range of 500 hr$^{-1}$ to 5,000 hr$^{-1}$. Incidentally, the space velocity is an equivalent in the normal temperature and pressure state (N.T.P.) of a value obtained by dividing an amount (L/hr) of the supply gas (b) supplied per one hour with an amount (L) of the catalyst (b) used in the secondary reaction.

By executing the above-described reaction, a reactant gas containing gaseous α-oxocarboxylate is obtained. More specifically, inconveniences involved in the conventional methods, for example, hydrolysis of α-oxocarboxylate due to the presence of water in the reaction system, can be avoided, thereby ensuring that α-oxocarboxylate can be produced at a higher yield than conventionally. A method for collection and isolation of gaseous α-oxocarboxylate are not particularly limited, and various known methods are applicable. By the method of the present invention, glyoxylate can be obtained from glyoxal, while pyruvate is obtained from pyruvic aldehyde.

Incidentally, the reactant gas containing, apart from unreacted oxygen gas and alcohol (b), α-oxocarboxylate contains formaldehyde, carbon monoxide, carbon dioxide, water, etc. as by-products that are produced by side reaction like combustion.

In the production of α-oxocarboxylate in accordance with the present invention, a reactant gas containing α-oxoaldehyde, resultant from the primary reaction, can be used as it is, as a material for the secondary reaction. In other words, in the production of α-oxocarboxylate in accordance with the present invention, the primary reaction and the secondary reaction can be executed successively. In this case, for example, a fixed-bed flow-through-type vapor phase reactor wherein a reactor used for the primary reaction and a reactor used for the secondary reaction are connected, that is, a so-called two-stage connection type, is preferable, though the reactor is not particularly limited. In the case where the fixed-bed flow-through-type vapor phase reactor, for example, is used, a reactant gas containing α-oxoaldehyde is obtained by flowing the supply gas (a) through the reactor at the first stage provided with the catalyst (a), and thereafter, the supply gas (b) is prepared by adding alcohol (b), oxygen, etc. to the reactant gas obtained and is flown through the reactor at the second stage provided with the catalyst (b), whereby a reactant gas containing α-oxocarboxylate is obtained.

Thus, by successively executing the primary reaction and the secondary reaction, or to state differently, by combining different vapor phase reactions in succession, α-oxocarboxylate can be produced from alkylene glycol through a substantially single stage without taking gaseous α-oxoaldehyde out of the reaction system.

In the case where the primary and secondary reactions are successively executed, the reactant gas resultant from the secondary reaction, gas resulting on separation of α-oxocarboxylate and other produced matters from the foregoing reactant gas, and gas containing alcohol uncollected upon separation and collection of alcohol from the foregoing gas can be re-used (recycled) as at least a part, or more preferably an entirety, of the supply gas (a) for the primary reaction. Produced matters including α-oxocarboxylate can be easily collected by condensing the reactant gas resultant from the secondary reaction with use of a condenser or the like. In this case, alcohol (a) used in the primary reaction contains unreacted alcohol (b) contained in the reactant gas resultant from the secondary reaction. Therefore, in the case where the same chemical compound is used as alcohol (a) and alcohol (b) and the foregoing recycling is carried out, production of α-oxocarboxylate from alkylene glycol is made further simpler and more efficient. More specifically, since complete separation of unreacted alcohol (b) is unnecessary upon re-use of a part or an entirety of the supply gas (a) for the primary reaction, costs for the separation can be cut.

As described above, a method of production of α-oxoaldehyde in accordance with the present invention is a method wherein alkylene glycol is oxidized in a vapor phase in the presence of alcohol (a), oxygen, and catalyst (a). By the foregoing method, the presence of alcohol (a) stabilizes α-oxoaldehyde, thereby resulting in that supply of, for example, water to obtain α-oxoaldehyde is unnecessary. Therefore, by the foregoing method, α-oxoaldehyde can be produced at a higher yield than conventionally, and further, an α-oxoaldehyde solution or gas at a higher concentration than conventionally can be stably obtained.

As described above, the method of production of α-oxocarboxylate in accordance with the present invention is a method wherein α-oxoaldehyde obtained by the above-described method, and alcohol (b) or olefin are oxidized in a vapor phase in the presence of oxygen and catalyst (b). By the foregoing method, inconveniences involved in the conventional methods can be avoided. More specifically, a 40 wt % aqueous solution of glyoxal available in the market need not be used as a material for the secondary reaction, and massive water need not be supplied to a reaction system when α-oxoaldehyde is obtained from the primary reaction, either, thereby ensuring that hydrolysis of α-oxocarboxylate in the secondary reaction can be avoided. Therefore, α-oxocarboxylate can be produced at a higher yield than conventionally.

The method of production of α-oxocarboxylate in accordance with the present invention is a method wherein, as the foregoing alcohol (a), a gas containing unreacted alcohol (b) that is contained in a reactant gas obtained by vapor phase oxidation of α-oxoaldehyde and the alcohol (b) is used. By the foregoing method, for example, a reactant gas resultant from the secondary reaction, a gas resulting on separation of produced matters from the reactant gas, or a gas containing alcohol (b) not collected upon separation and collection of alcohol (b) from the foregoing gas, is re-used as a part, or preferably an entirety, of the supply gas (a) for the primary reaction. In this case, since the alcohol (a) re-used contains unreacted alcohol (b), production of α-oxocarboxylate from alkylene glycol is made simpler and more efficient in the case where one and same chemical compound is used as the alcohol (a) and the alcohol (b) and the re-use as described is executed.

The present invention will be described more specifically below with reference to examples and comparative examples. It should be noted that the scope of the present invention is not limited to these examples. In the following examples and comparative examples, executed were a reaction (primary reaction) in which glyoxal (hereinafter referred to as GLO) as α-oxoaldehyde is obtained from ethylene glycol (hereinafter referred to as EG) as alkylene glycol, and in succession from the primary reaction, a reaction (secondary reaction) in which methyl glyoxylate (hereinafter referred to as MGO) as α-oxocarboxylate is obtained from GLO.

A reactant gas resultant from the primary reaction, cooled to a freezing point, was collected with water, and was analyzed, using a high speed liquid chromatography equipped with a differential refractometer detector under predetermined conditions, adopting the internal standard method. In other words, unreacted EG contained in the foregoing reactant gas and GLO produced were quantified.

Further, the reactant gas resultant from the secondary reaction, cooled to a freezing point, was collected with acetonitrile, and was analyzed, using a high speed liquid chromatography equipped with a differential refractometer detector and a gaschromatography equipped with an FID (flame ionization detector) under predetermined conditions, adopting the internal standard method. In other words, unreacted GLO contained in the foregoing reactant gas was quantified using the high speed liquid chromatography, while produced MGO contained in the reactant gas was quantified using the gaschromatography.

Conversion, yield, and selectivity shown in the descriptions of the examples and comparative examples were calculated, using results of the foregoing quantification, according to the following formulas:

The reacted EG (mol)=EG supplied (mol)−unreacted EG (mol)

The conversion of EG (%)=(reacted EG (mol)/EG supplied (mol))×100

The yield of GLO (%) = (GLO produced from the primary reaction (mol) / EG supplied (mol)) × 100

The reacted GLO (mol)=GLO supplied (mol)−unreacted GLO (mol)

The conversion of GLO (%)=(reacted GLO (mol)/GLO supplied (mol))×100

The selectivity of MGO (%)=(MGO produced (mol)/reacted GLO (mol))×100

The yield of MGO with respect to EG (%)=(MGO produced (mol)/EG supplied (mol))×100

EXAMPLE 1

GLO was obtained from EG through the primary reaction. An SUS (Stainless Steel) pipe with an inner diameter of 12 mm was used as a reaction pipe (primary reactor), in which placed (laminated) was 15 g of metallic silver (electrolytic silver with a particle diameter of 20 to 30 mesh, available from Yokohama Metal Co., Ltd.) as catalyst (a). Further, on a gas inlet side of the reaction pipe, a vaporizer was attached so as to heat to a predetermined temperature a supply gas (a) to be supplied to the reaction pipe. Further, the reaction pipe has a heat insulating material wound therearound for heat retention, so that the temperature of a catalyst layer during the primary reaction (reaction temperature) would be kept at a predetermined temperature. In other words, heat retention was ensured so that the primary reaction proceeded under conditions substantially equivalent to those of adiabatic reaction.

Proportions of EG, oxygen, methanol as alcohol (a), and water in the supply gas (a) were set, in this order, 4.0 vol %, 4.8 vol %, 3.0 vol %, and 0 vol %, respectively (nitrogen gas accounted for the rest, and the total was 100 vol %: this is hereinafter referred to as nitrogen gas balance). To the foregoing supply gas (a), triethyl phosphite as a phosphorus-containing compound was added so that a ratio of phosphorus to EG became 60 ppm.

The supply gas (a) of the foregoing composition was continuously supplied to the reaction pipe at a space velocity (SV) of 45,000 hr$^{-1}$, so that the primary reaction occurred. The reaction temperature, that is, the temperature of the catalyst layer, reached 570° C. Main reaction conditions are shown in Table 1.

A composition of a reactant gas obtained was analyzed in the aforementioned manner. Consequently, the conversion of EG was 100%, and the yield of GLO was 88%. The result is shown in Table 3.

EXAMPLE 2

The primary reaction was made to take place under the same conditions as in Example 1 except that the proportions of EG, oxygen, methanol, and water in the supply gas (a) were changed to, in this order, 4.0 vol %, 4.8 vol %, 4.0 vol %, and 0 vol %, respectively (nitrogen gas balance). The temperature of the catalyst layer reached 565° C. Main reaction conditions are shown in Table 1. Consequently, the conversion of EG was 100%, and the yield of GLO was 89%. The result is shown in Table 3. Incidentally, a very small amount of glycol aldehyde produced as a reaction intermediate (by-product) was detected. An amount of methanol lost by side reaction such as combustion was 10 wt % of an amount supplied.

Comparative Example 1

A comparison-use supply gas (a) containing no alcohol (a) was used in the primary reaction. In other words, the primary reaction was made to take place under the same conditions as in Example 1 except that the proportions of EG, oxygen, methanol, and water in the comparison-use supply gas (a) were set to, in this order, 4.0 vol %, 4.8 vol %, 0 vol %, and 0 vol %, respectively (nitrogen gas balance). The temperature of the catalyst layer reached 586° C. Main reaction conditions are shown in Table 1. Consequently, the conversion of EG was 100%, but the yield of GLO was as low as 77%. The result is shown in Table 3.

Comparative Example 2

A comparison-use supply gas (a) containing water instead of alcohol (a) was used in the primary reaction. In other words, the primary reaction was made to take place under the same conditions as in Example 1 except that the proportions of EG, oxygen, methanol, and water in the comparison-use supply gas (a) were set to, in this order, 4.0 vol %, 4.8 vol %, 0 vol %, and 3.0 vol %, respectively (nitrogen gas balance). The temperature of the catalyst layer reached 583° C. Main reaction conditions are shown in Table 1. Consequently, the conversion of EG was 100%, but the yield of GLO was as low as 79%. The result is shown in Table 3.

EXAMPLE 3

The primary reaction was made to take place under the same conditions as in Example 1 except that the proportions of EG, oxygen, methanol, and water in the supply gas (a) were set to, in this order, 4.0 vol %, 4.8 vol %, 20.0 vol %, and 3.0 vol %, respectively (nitrogen gas balance), and that triethyl phosphite was added to the supply gas (a) so that a ratio of phosphorus to EG became 80 ppm. The temperature of the catalyst layer reached 569° C. Main reaction conditions are shown in Table 1. Consequently, the conversion of EG was 100%, and the yield of GLO was 89%. The result is shown in Table 3.

EXAMPLE 4

The primary reaction was made to take place under the same conditions as in Example 1 except that the proportions of EG, oxygen, methanol, and water in the supply gas (a) were changed to, in this order, 4.0 vol %, 4.8 vol %, 3.0 vol %, and 1.0 vol %, respectively (nitrogen gas balance). The temperature of the catalyst layer reached 567° C. Main reaction conditions are shown in Table 1. Consequently, the conversion of EG was 100%, and the yield of GLO was 89%. The result is shown in Table 3.

EXAMPLE 5

The primary reaction was made to take place under the same conditions as in Example 1 except that the proportions of EG, oxygen, methanol, and water in the supply gas (a) were changed to, in this order, 4.0 vol %, 4.8 vol %, 1.0 vol %, and 0 vol %, respectively (nitrogen gas balance). The temperature of the catalyst layer reached 583° C. Main reaction conditions are shown in Table 1. Consequently, the conversion of EG was 100%, and the yield of GLO was 82%. The result is shown in Table 3. A GLO aqueous solution obtained had a concentration of about 58 wt %, which is higher than the concentration of a GLO aqueous solution available from the market (40 wt %). In other words, a GLO aqueous solution with a higher concentration than that available from the market could be obtained stably.

EXAMPLE 6

The primary reaction was made to take place under the same conditions as in Example 1 except that the proportions of EG, oxygen, methanol, and water in the supply gas (a) were changed to, in this order, 4.0 vol %, 4.0 vol %, 4.0 vol %, and 0 vol %, respectively (nitrogen gas balance). The temperature of the catalyst layer reached 573° C. Main reaction conditions are shown in Table 1. Consequently, the conversion of EG was 99%, and the yield of GLO was 85%. The result is shown in Table 3.

EXAMPLE 7

The primary reaction was made to take place under the same conditions as in Example 1 except that the proportions of EG, oxygen, methanol, and water in the supply gas (a) were changed to, in this order, 4.0 vol %, 6.0 vol %, 4.0 vol %, and 0 vol %, respectively (nitrogen gas balance). The temperature of the catalyst layer reached 572° C. Main reaction conditions are shown in Table 1. Consequently, the conversion of EG was 100%, and the yield of GLO was 89%. The result is shown in Table 3.

EXAMPLE 8

The primary reaction was made to take place under the same conditions as in Example 1 except that the proportions of EG, oxygen, methanol, and water in the supply gas (a) were changed to, in this order, 3.0 vol %, 4.0 vol %, 3.0 vol %, and 0 vol %, respectively (nitrogen gas balance). The temperature of the catalyst layer reached 557° C. Main reaction conditions are shown in Table 2. Consequently, the conversion of EG was 99%, and the yield of GLO was 86%. The result is shown in Table 3.

EXAMPLE 9

The primary reaction was made to take place under the same conditions as in Example 1 except that the proportions of EG, oxygen, methanol, and water in the supply gas (a) were changed to, in this order, 5.0 vol %, 6.0 vol %, 4.0 vol %, and 0 vol %, respectively (nitrogen gas balance). The temperature of the catalyst layer reached 588° C. Main reaction conditions are shown in Table 2. Consequently, the conversion of EG was 100%, and the yield of GLO was 84%. The result is shown in Table 3.

EXAMPLE 10

The primary reaction was made to take place under the same conditions as in Example 1 except that the proportions of EG, oxygen, methanol, and water in the supply gas (a) were changed to, in this order, 5.0 vol %, 6.0 vol %, 4.0 vol %, and 1.0 vol %, respectively (nitrogen gas balance). The temperature of the catalyst layer reached 587° C. Main reaction conditions are shown in Table 2. Consequently, the conversion of EG was 100%, and the yield of GLO was 84%. The result is shown in Table 3.

EXAMPLE 11

GLO was obtained from EG through the primary reaction in an identical manner to that in Example 1, except that 10 g of metallic silver (electrolytic silver available from Yokohama Metal Co., Ltd.) with a particle diameter of 20 to 30 mesh was placed (laminated) on the gas inlet side in the reaction pipe, while log of metallic silver (the same as above) with a particle diameter of 16 to 20 mesh was placed (laminated) on the gas outlet side in the reaction pipe.

The primary reaction was made to take place under the same conditions as in Example 1 except that the proportions of EG, oxygen, methanol, and water in the supply gas (a) were changed to, in this order, 4.0 vol %, 4.8 vol %, 4.0 vol %, and 0 vol %, respectively (nitrogen gas balance). The temperature of the catalyst layer reached 555° C. Main reaction conditions are shown in Table 2. Consequently, the conversion of EG was 100%, and the yield of GLO was 91%. The result is shown in Table 3. A GLO aqueous solution obtained had a concentration of about 56 wt %, which is higher than the concentration of a GLO aqueous solution available from the market (40 wt %). In other words, a GLO aqueous solution with a higher concentration than that available from the market could be obtained stably.

EXAMPLE 12

The primary reaction was made to take place under the same conditions as in Example 11 except that the supply gas (a) was continuously supplied to the reaction pipe so that the space velocity (SV) became 100,000 $hr^{-1}$. The temperature of the catalyst layer reached 554° C. Main reaction conditions are shown in Table 2. Consequently, the conversion of EG was 100% and the yield of GLO was 90%. The result is shown in Table 3.

EXAMPLE 13

The primary reaction was made to take place under the same conditions as in Example 11 except that an amount of metallic silver placed on the gas outlet side in the reaction pipe was set to 5 g and that the supply gas (a) was continuously supplied to the reaction pipe so that the space velocity (SV) became 70,000 $hr^{-1}$. The temperature of the catalyst layer reached 555° C. Main reaction conditions are shown in Table 2. Consequently, the conversion of EG was 99%, and the yield of GLO was 90%. The result is shown in Table 3. Incidentally, a very small amount of glycol aldehyde produced as a reaction intermediate (by-product) was detected. An amount of methanol lost by side reaction such as combustion was 13 wt % of an amount supplied.

EXAMPLE 14

The primary reaction was made to take place under the same conditions as in Example 11 except that an amount of metallic silver placed on the gas outlet side in the reaction pipe was set to 5 g, that the proportions of EG, oxygen, methanol, and water in the supply gas (a) were changed to, in this order, 4.0 vol %, 4.8 vol %, 20.0 vol %, and 0 vol %, respectively (nitrogen gas balance), and that triethyl phosphite was added to the supply gas (a) so that a ratio of phosphorus to EG became 100 ppm. The temperature of the catalyst layer reached 558° C. Main reaction conditions are shown in Table 2. Consequently, the conversion of EG was 100%, and the yield of GLO was 91%. The result is shown in Table 3.

EXAMPLE 15

Metallic silver modified with use of phosphorus-containing compound as catalyst (a) was prepared in the following manner. More specifically, 85 wt % aqueous solution of phosphoric acid was added to metallic silver (electrolytic silver available from Yokohama Metal Co., Ltd.) with a particle diameter of 20 to 30 mesh so that a ratio of phosphorus to silver became 200 ppm. Thus, metallic silver was made to carry phosphorus. The metallic silver carrying phosphorus was dried in air at 120° C., and thereafter, calcined in air at 600° C. for 3 hours. In this way, metallic silver modified with use of phosphoric acid (phosphorus-containing compound) was prepared, as catalyst (a).

Using the foregoing metallic silver as catalyst (a), GLO was obtained from EG through the primary reaction performed in an identical manner to that in Example 1. More specifically, the primary reaction was made to take place under the same conditions as in Example 1 except that the proportions of EG, oxygen, methanol, and water in the supply gas (a) were changed to, in this order, 4.0 vol %, 4.8 vol %, 4.0 vol %, and 1.0 vol %, respectively (nitrogen gas balance), that an amount of metallic silver placed in the reaction pipe was set to 5 g, and that a phosphorus-containing compound was not supplied along with the supply gas (a). The temperature of the catalyst layer reached 590° C. Main reaction conditions are shown in Table 2. Consequently, the conversion of EG was 100%, and the yield of GLO was 79%. The result is shown in Table 3.

EXAMPLE 16

Metallic silver modified with use of phosphoric acid was prepared through the same operation as that in Example 15 except that 85 wt % aqueous solution of phosphoric acid was added to metallic silver so that a ratio of phosphorus to silver became 80 ppm.

Using as catalyst (a) the metallic silver thus obtained, GLO was obtained from EG through the primary reaction performed in an identical manner to that in Example 1. More specifically, the primary reaction was made to take place under the same conditions as in Example 1 except that an amount of metallic silver placed in the reaction pipe was set to 5 g, that the proportions of EG, oxygen, methanol, and water in the supply gas (a) were changed to, in this order, 4.0 vol %, 4.8 vol %, 4.0 vol %, and 1.0 vol %, respectively (nitrogen gas balance). The temperature of the catalyst layer reached 578° C. Main reaction conditions are shown in Table 2. Consequently, the conversion of EG was 100%, and the yield of GLO was 82%. The result is shown in Table 3.

TABLE 1

| | COMPOSITION OF SUPPLY GAS (a) (vol %, NITROGEN GAS BALANCE) | | | | AMOUNT OF SUPPLIED PHOSPHORUS | SPACE VELOCITY SV | CATALYST (a) | | TEMPERATURE OF CATALYST LAYER |
|---|---|---|---|---|---|---|---|---|---|
| | | | | | | | PARTICLE DIAMETER | AMOUNT | |
| | EG | O$_2$ | MeOH | H$_2$O | (ppm) | (hr$^{-1}$) | (mesh) | (g) | (° C.) |
| EX. 1 | 4.0 | 4.8 | 3.0 | 0 | 60 | 45000 | 20–30 | 15 | 570 |
| EX. 2 | 4.0 | 4.8 | 4.0 | 0 | 60 | 45000 | 20–30 | 15 | 565 |
| COMP. EX. 1 | 4.0 | 4.8 | 0 | 0 | 60 | 45000 | 20–30 | 15 | 586 |
| COMP. EX. 2 | 4.0 | 4.8 | 0 | 3.0 | 60 | 45000 | 20–30 | 15 | 583 |
| EX. 3 | 4.0 | 4.8 | 20.0 | 3.0 | 80 | 45000 | 20–30 | 15 | 569 |
| EX. 4 | 4.0 | 4.8 | 3.0 | 1.0 | 60 | 45000 | 20–30 | 15 | 567 |
| EX. 5 | 4.0 | 4.8 | 1.0 | 0 | 60 | 45000 | 20–30 | 15 | 583 |
| EX. 6 | 4.0 | 4.0 | 4.0 | 0 | 60 | 45000 | 20–30 | 15 | 573 |
| EX. 7 | 4.0 | 6.0 | 4.0 | 0 | 60 | 45000 | 20–30 | 15 | 572 |

TABLE 2

| | COMPOSITION OF SUPPLY GAS (a) (vol %, NITROGEN GAS BALANCE) | | | | AMOUNT OF SUPPLIED PHOSPHORUS | SPACE VELOCITY SV | CATALYST (a) | | TEMPERATURE OF CATALYST LAYER |
|---|---|---|---|---|---|---|---|---|---|
| | | | | | | | PARTICLE DIAMETER | AMOUNT | |
| | EG | O$_2$ | MeOH | H$_2$O | (ppm) | (hr$^{-1}$) | (mesh) | (g) | (° C.) |
| EX. 8 | 3.0 | 4.0 | 3.0 | 0 | 60 | 45000 | 20–30 | 15 | 557 |
| EX. 9 | 5.0 | 6.0 | 4.0 | 0 | 60 | 45000 | 20–30 | 15 | 588 |
| EX. 10 | 5.0 | 6.0 | 4.0 | 1.0 | 60 | 45000 | 20–30 | 15 | 587 |
| EX. 11 | 4.0 | 4.8 | 4.0 | 0 | 60 | 45000 | 20–30 16–20 | 10 10 | 555 |
| EX. 12 | 4.0 | 4.8 | 4.0 | 0 | 60 | 100000 | 20–30 16–20 | 10 | 554 |
| EX. 13 | 4.0 | 4.8 | 4.0 | 0 | 60 | 70000 | 20–30 16–20 | 10 | 555 |
| EX. 14 | 4.0 | 4.8 | 20.0 | 0 | 100 | 45000 | 20–30 16–20 | 10 | 558 |
| EX. 15 | 4.0 | 4.8 | 4.0 | 1.0 | 0 | 45000 | 20–30 | 5 | 590 |
| EX. 16 | 4.0 | 4.8 | 4.0 | 1.0 | 60 | 45000 | 20–30 | 5 | 578 |

TABLE 3

| | CONVERSION OF EG (%) | YIELD OF GLO (%) |
|---|---|---|
| EXAMPLE 1 | 100 | 88 |
| EXAMPLE 2 | 100 | 89 |
| COMPARATIVE EX. 1 | 100 | 77 |
| COMPARATIVE EX. 2 | 100 | 79 |
| EXAMPLE 3 | 100 | 89 |
| EXAMPLE 4 | 100 | 89 |
| EXAMPLE 5 | 100 | 82 |
| EXAMPLE 6 | 99 | 85 |
| EXAMPLE 7 | 100 | 89 |
| EXAMPLE 8 | 99 | 86 |
| EXAMPLE 9 | 100 | 84 |
| EXAMPLE 10 | 100 | 84 |
| EXAMPLE 11 | 100 | 91 |
| EXAMPLE 12 | 100 | 90 |
| EXAMPLE 13 | 99 | 90 |
| EXAMPLE 14 | 100 | 91 |
| EXAMPLE 15 | 100 | 79 |
| EXAMPLE 16 | 100 | 82 |

EXAMPLE 17

MGO was obtained from GLO through the secondary reaction. Titania-added iron phosphate as catalyst (b) was prepared in the following manner.

Namely, iron phosphate (FePO$_4$.4H$_2$O: reagent available from Katayama Chemical Industries Ltd.) as a metallic phosphate and anatase-type titanium dioxide (TiO$_2$: reagent available from Wako Pure Chemical Industries, Ltd.) as an inorganic oxide were well mixed in a mortar, and a moisture thereof was adjusted with water. A ratio of phosphorus to iron in iron phosphate was 1/1. An amount of the titanium dioxide added was set so that titania accounted for 30 wt % in resultant titania-added iron phosphate.

Subsequently, a mixture obtained was molded using a so-called latch forming plate, and was dried in air at 120° C. A resultant cylindrical pellet with a diameter of 5 mm and a length of 6 mm was sintered in air at 500° C. for 3 hours. In this way, titania-added iron phosphate as catalyst (b) was prepared. Then, a predetermined amount of titania-added iron phosphate was placed in the reactor for the secondary reaction (hereinafter referred to as secondary reactor).

Reaction conditions of the primary reaction were set identical to those in the case of Example 2. Methanol was used as alcohol (b). The proportions of GLO, oxygen, and methanol in the supply gas (b) prepared in the vaporizer connected to the secondary reactor and to be supplied to the secondary reactor were set to, in this order, 3.0 vol %, 4.0 vol %, and 15.0 vol %, respectively (nitrogen gas balance). Incidentally, regarding oxygen and methanol, in order that the supply gas (b) with the foregoing composition was obtained, oxygen and methanol contained in the reactant gas resultant from the primary reaction were quantified, and the same were supplied to the vaporizer for shortages only, through a gas supply inlet of the secondary reactor.

The supply gas (b) of the foregoing composition was continuously supplied to the secondary reactor at a space velocity (SV) of 1,300 hr$^{-1}$, so that the secondary reaction took place. A reaction temperature was set to 250° C.

A composition of the reactant gas obtained was analyzed in the aforementioned manner. Consequently, the conversion of GLO was 100%, the selectivity of MGO was 78%, and the yield of MGO with respect to EG was 71%. Main reaction conditions and the result of the reaction are shown in Table 4.

EXAMPLE 18

The secondary reaction was made to take place under the same conditions as those in Example 17 except that the reaction conditions in Example 11 were adopted as reaction conditions of the primary reaction. More specifically, the secondary reaction was made to take place at respective molar ratios of oxygen and methanol to GLO produced through the primary reaction that were made to agree with the molar ratios calculated from the ratios in Example 17 (oxygen/GLO=1.3 methanol/GLO=5.0). Consequently, the conversion of GLO was 100%, the selectivity of MGO was 78%, and the yield of MGO with respect to EG was 69%. Main reaction conditions and the result of the reaction are shown in Table 4.

EXAMPLE 19

MGO was obtained from GLO that was obtained from EG, through the primary and secondary reactions that were successively executed, with use of alcohol (a) and alcohol (b) which were the same compound, while gas resultant from separation of produced matters from the reactant gas obtained through the secondary reaction (hereinafter referred to as recycled gas) was re-used as a part of the supply gas (a) used in the primary reaction. Incidentally, FIG. 1 is a block diagram schematically illustrating a device for and a process of reaction in the present example.

To be more specific, an SUS (Stainless Steel) pipe with an inner diameter of 1 inch was used as a primary-reaction-use reaction pipe (primary reactor), in which placed was 88 g of metallic silver (electrolytic silver with a particle diameter of 20 to 30 mesh, available from Yokohama Metal Co., Ltd.) as catalyst (a). Further, on a gas inlet side of the reaction pipe, a preheater for heating the supply gas (a) to be supplied to the reaction pipe to a predetermined temperature was attached. To the preheater, a vaporizer for vaporizing EG to be supplied to the preheater was attached. Further, the reaction pipe has an insulating material wound therearound for heat retention, so that the temperature of a catalyst layer during the primary reaction (reaction temperature) would be kept at a predetermined temperature. In other words, heat retention was ensured so that the primary reaction proceeded under conditions substantially equivalent to those of adiabatic reaction.

The supply gas (a) is a mixture gas of a recycled gas (containing methanol), vaporized EG, and air. The reaction conditions in Example 4 were adopted as reaction conditions of the primary reaction. Therefore, the proportions of EG, oxygen, methanol as alcohol (a), and water in the supply gas (a) were set to, in this order, 4.0 vol %, 4.8 vol %, 3.0 vol %, and 1.0 vol %, respectively (nitrogen gas balance). In other words, in order that the supply gas (a) with the foregoing composition was constantly obtained, oxygen, methanol, and the like contained in the recycled gas were quantified, and air was supplied thereto for oxygen shortage only. Triethyl phosphite was preliminarily added to EG supplied to the foregoing vaporizer so that a ratio of phosphorus to EG became 60 ppm.

On the other hand, a predetermined amount of titania-added iron phosphate as prepared in Example 17 as catalyst (b) was placed in the secondary reactor. Further, a condenser for condensing the resultant reactant gas was attached on a gas outlet side of the secondary reactor, so that produced matters including MGO were separated in a form of condensed liquid from the reactant gas. A temperature of the recycled gas was adjusted so as to become 15° C. at the outlet of the condenser. A part of the recycled gas was purged, and the rest was continuously supplied to the primary-reaction-use reaction pipe. Incidentally, the concentration of unreacted methanol contained in the recycled gas was adjusted by control of a temperature of cooling medium used in the condenser.

Methanol was used as alcohol (b). Proportions of GLO, oxygen, and methanol in the supply gas (b) were set to, in this order, 2.8 vol %, 3.7 vol %, and 14.0 vol %, respectively (nitrogen gas balance). Incidentally, regarding oxygen (air) and methanol, oxygen and methanol contained in the reactant gas obtained through the primary reaction were quantified and the same were supplied to a vaporizing chamber for shortages only, so that the supply gas (b) with the foregoing composition could be obtained. The vaporizing chamber was attached on a gas inlet side of the secondary reactor so that methanol was vaporized, while a mixture gas containing the reactant gas resultant from the primary reaction, vaporized methanol, and air was formed and continuously supplied to the secondary reactor.

The supply gas (a) of the foregoing composition was continuously supplied to the reaction pipe at a space velocity (SV) of 45,000 hr$^{-1}$ so that the primary reaction took place, while the supply gas (b) of the foregoing composition was continuously supplied to the secondary reactor at a space velocity of 1,300 hr$^{-1}$ so that the secondary reaction took place. The reaction temperature of the secondary reaction was set to 250° C.

As a result of analysis of the composition of the reactant gas resultant from the primary reaction in the aforementioned manner, the conversion of EG was 100%, and the yield of GLO was 88%. On the other hand, the composition of the reactant gas resultant from the secondary reaction was analyzed in the aforementioned manner. As a result, the conversion of GLO was 100%, the selectivity of MGO was 78%, and the yield of MGO with respect to EG was 69%. Main reaction conditions and the result of the reaction are shown in Table 4.

EXAMPLE 20

The secondary reaction was made to take place under the same conditions as those in Example 19 except that the reaction conditions in Example 5 were adopted as reaction conditions of the primary reaction. Therefore, the primary and secondary reactions were successively executed.

The proportions of EG, oxygen, methanol, and water in the supply gas (a) were set to, in this order, 4.0 vol %, 4.8 vol %, 1.0 vol %, and 0 vol %, respectively (nitrogen gas balance). The proportions of GLO, oxygen, and methanol in the supply gas (b) were set to, in this order, 2.6 vol %, 3.6 vol %, and 13.0 vol %, respectively (nitrogen gas balance). The temperature of the recycled gas in the secondary reaction was set to 0° C. so that the concentration of unreacted methanol contained in the recycled gas was adjusted as above.

As a result of analysis of the composition of the reactant gas resultant from the primary reaction in the aforementioned manner, the conversion of EG was 100%, and the yield of GLO was 82%. On the other hand, the composition of the reactant gas resultant from the secondary reaction was analyzed in the aforementioned manner. As a result, the conversion of GLO was 100%, the selectivity of MGO was 78%, and the yield of MGO with respect to EG was 64%. Main reaction conditions and the result of the reaction are shown in Table 4.

Comparative Example 3

The secondary reaction was made to take place under the same conditions as those in Example 19 except that the reaction conditions in Comparative Example 1 were adopted as reaction conditions of the primary reaction.

Therefore, the primary and secondary reactions were successively executed. The recycled gas, however, was not put in use.

The proportions of EG, oxygen, methanol, and water in the comparison-use supply gas (a) were set to, in this order, 4.0 vol %, 4.8 vol %, 0 vol %, and 0 vol %, respectively (nitrogen gas balance). The proportions of GLO, oxygen, and methanol in the comparison-use supply gas (b) were set to, in this order, 2.2 vol %, 3.0 vol %, and 11.0 vol %, respectively (nitrogen gas balance).

As a result of analysis of the composition of the reactant gas resultant from the primary reaction in the aforementioned manner, the conversion of EG was 100%, and the yield of GLO was 76%. On the other hand, the composition of the reactant gas resultant from the secondary reaction was analized in the aforementioned manner. As a result, the conversion of GLO was 100%, and the selectivity of MGO was 77%, but the yield of MGO with respect to EG was as low as 59%. Main reaction conditions and the result of the reaction are shown in Table 4.

(together with other materials) of massive water to obtain α-oxoaldehyde, the aforementioned method does not require supply of water or the like for obtaining the α-oxoaldehyde because of stabilization of α-oxoaldehyde by the presence of alcohol (a). Therefore, the aforementioned method has the following effect: α-oxoaldehyde can be produced at a higher yield than conventionally, and besides, an oxoaldehyde solution or gas at a higher concentration than conventionally can be stably obtained.

Thus, by the method of production of α-oxoaldehyde in accordance with the present invention, the following effect can be achieved: α-oxoaldehyde can be produced at a further higher yield.

By the method of production of α-oxocarboxylate in accordance with the present invention, inconveniences involved in the conventional methods, for example, hydrolysis of α-oxocarboxylate due to the presence of water in a reaction system, can be obviated. Therefore, the following effect can be achieved: α-oxocarboxylate can be produced at a higher yield than conventionally.

According to the method of production of α-oxocarboxylate in accordance with the present invention, alcohol (a) need not be removed from α-oxoaldehyde prior to production of α-oxocarboxylate. Therefore, the following effect can be achieved: α-oxocarboxylate can be produced more easily.

According to the method of production of α-oxocarboxylate in accordance with the present invention, reactant gas resultant from vapor phase oxidation of α-oxoaldehyde and alcohol (b), gas resultant from separation of produced matters such as α-oxocarboxylate from the foregoing reactant gas, or gas containing alcohol uncollected upon separation and collection of alcohol from the foregoing gas, can be re-used as a part, or preferably an entirety, of gas used for vapor phase oxidation of alkylene glycol (gas

TABLE 4

| PRIMARY REACTION | | COMPOSITION OF SUPPLY GAS (b) | | | SPACE | | | | YIELD |
| --- | --- | --- | --- | --- | --- | --- | --- | --- | --- |
| EXAMPLE | YIELD OF GLO | (vol %, NITROGEN GAS BALANCE) | | | VELOCITY SV | REACTION TEMPERATURE | CONVERSION OF GLO | SELECTIVITY OF MGO | OF MGO |
| (NO.) | (%) | GLO | $O_2$ | MeOH | $(hr^{-1})$ | (° C.) | (%) | (%) | (%) |
| EX. 17 | 2 | 89 | 3.0 | 4.0 | 15.0 | 1300 | 250 | 100 | 78 | 69 |
| EX. 18 | 11 | 91 | 3.2 | 4.3 | 16.0 | 1300 | 250 | 100 | 78 | 71 |
| EX. 19 | 4 | 88 | 2.8 | 3.7 | 14.0 | 1300 | 250 | 100 | 78 | 69 |
| EX. 20 | 5 | 82 | 2.6 | 3.6 | 13.0 | 1300 | 250 | 100 | 78 | 64 |
| COMP. EX. 3 | COMP. EX. 1 | 76 | 2.2 | 3.0 | 11.0 | 1300 | 250 | 100 | 77 | 59 |

Incidentally, the concrete embodiment and examples thus described in the "Best Mode for Carrying Out the Invention" are only intended to make the technical contents of the present invention explicit, and it will be obvious that the present invention may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

By the method of production of α-oxoaldehyde in accordance with the present invention, α-oxoaldehyde can be produced at a higher yield than conventionally. Further, while the conventional method requires, for example, supply containing alkylene glycol and alcohol (a)). In this case, since the alcohol (a) re-used contains unreacted alcohol (b), the following effect can be achieved in the case where the same compound is used as the alcohol (a) and the alcohol (b) and the above-described re-usage is executed: α-oxocarboxylate can be more easily and efficiently produced from alkylene glycol.

What is claimed is:

1. A method of production of α-oxoaldehyde, comprising the step of oxidizing alkylene glycol in a vapor phase in the presence of alcohol (a), oxygen and a catalyst (a), wherein alcohol (a) is not an alkylene glycol.

2. The method of production of α-oxoaldehyde as set forth in claim 1, wherein a molar ratio of the alkylene glycol to the alcohol (a) is in a range of 1/100 to 5/1.

3. The method of production of α-oxoaldehyde as set forth in claim 1, wherein proportions of the alkylene glycol, the oxygen, and the alcohol (a) are, in this order, 1 percent by volume to 10 percent by volume, 1 percent by volume to 10 percent by volume, and 0.01 percent by volume to 30 percent by volume, respectively.

4. The method of production of α-oxoaldehyde as set forth in claim 1, wherein the alkylene glycol is 1,2-diol.

5. The method of production of α-oxoaldehyde as set forth in claim 1, wherein the catalyst (a) is metallic silver, and/or metallic silver modified with use of a phosphorus-containing compound.

6. A method of production of α-oxocarboxylate, comprising the steps of:

oxidizing the alkylene glycol in a vapor phase in the presence of alcohol (a), oxygen and a catalyst (a), wherein alcohol (a) is not an alkylene glycol so as to obtain α-oxoaldehyde; and oxidizing the α-oxoaldehyde, and alcohol (b) or olefin, in a vapor phase in the presence of oxygen and a catalyst (b).

7. The method of production of α-oxocarboxylate as set forth in claim 6, wherein one same compound is used as the alcohol (a) and the alcohol (b).

8. The method of production of α-oxocarboxylate as set forth in claim 6, wherein the alcohol (a) contains unreacted alcohol (b) that is contained in a reactant gas resultant from the vapor phase oxidation of the α-oxoaldehyde and the alcohol (b).

9. The method of production of α-oxocarboxylate as set forth in claim 6 wherein the catalyst (a) is a metallic catalyst and/or an oxide catalyst, and the catalyst (b) is a catalyst containing a phosphorus-containing inorganic oxide.

10. The method of production of α-oxoaldehyde as set forth in claim 1, wherein the catalyst (a) is a metallic catalyst and/or an oxide catalyst.

* * * * *